United States Patent
Nogueira et al.

(10) Patent No.: US 9,987,215 B2
(45) Date of Patent: Jun. 5, 2018

(54) STRUCTURING OF COSMETIC COMPOSTION USING ORGANOGELS

(71) Applicant: CHEMYUNION QUIMICA LTDA., Sorocaba (BR)

(72) Inventors: Cecilia Nogueira, Sorocaba (BR); Cristiane Rodrigues da Silva Pacheco, Sao Paulo (BR); Daniel Barrera Arellano, Paulinia (BR); Daniele Cristina Zulim Botega, Sorocaba (BR); Mario Luiz Mathias Netto, Tiete (BR)

(73) Assignee: CHEMYUNION QUIMICA LTDA., Sao Paulo (BR)

( * ) Notice: Subject to any disclaimer, the term of this patent is extended or adjusted under 35 U.S.C. 154(b) by 0 days. days.

(21) Appl. No.: 14/778,862

(22) PCT Filed: Mar. 22, 2013

(86) PCT No.: PCT/IB2013/052296
§ 371 (c)(1),
(2) Date: Sep. 21, 2015

(87) PCT Pub. No.: WO2014/147447
PCT Pub. Date: Sep. 25, 2014

(65) Prior Publication Data
US 2016/0045426 A1 Feb. 18, 2016

(51) Int. Cl.
| A61K 8/92 | (2006.01) |
| A61K 8/37 | (2006.01) |
| A61Q 19/00 | (2006.01) |
| A61K 8/02 | (2006.01) |
| A61K 8/04 | (2006.01) |
| A61Q 17/04 | (2006.01) |
| A61K 8/06 | (2006.01) |

(52) U.S. Cl.
CPC ............ *A61K 8/922* (2013.01); *A61K 8/0295* (2013.01); *A61K 8/042* (2013.01); *A61K 8/06* (2013.01); *A61K 8/375* (2013.01); *A61Q 17/04* (2013.01); *A61Q 19/00* (2013.01)

(58) Field of Classification Search
CPC ...... A61K 8/0295; A61K 8/042; A61K 8/375; A61K 8/922; A61K 8/553; A61K 8/37; A61K 47/24; A61K 8/676; A61K 8/678; A61K 8/73; A61K 9/1274; A61K 2800/31; A61K 2800/522; A61K 47/10; A61K 47/14; A61K 8/06; A61K 8/062; A61K 8/345; A61K 8/365; A61K 8/42; A61K 8/46; A61K 8/466; A61K 8/4913; A61K 8/60; A61K 8/63; A61K 8/671; A61K 8/891; A61K 8/893; A61K 8/898; A61K 8/90; A61K 9/0014; A61Q 17/04; A61Q 19/00; A61Q 17/005; A61Q 19/08; A61Q 1/06; A61Q 19/004; A61Q 19/005; A61Q 19/02; A61Q 1/02; A61Q 1/10; A61Q 3/00; A61Q 5/00
See application file for complete search history.

(56) References Cited

U.S. PATENT DOCUMENTS

| 5,639,740 | A | * | 6/1997 | Crandall | ............... A61K 8/365 514/159 |
| 6,342,238 | B1 | * | 1/2002 | Simonnet | ............... A61K 8/042 264/4.1 |
| 2006/0078577 | A1 | | 4/2006 | Dechow | |
| 2006/0110355 | A1 | * | 5/2006 | Blin | ................. A61K 8/37 424/70.23 |
| 2007/0093619 | A1 | * | 4/2007 | Bui | ................. A61K 8/891 525/477 |
| 2011/0250299 | A1 | * | 10/2011 | Baseeth | ................ A23D 7/011 424/729 |

OTHER PUBLICATIONS

International Preliminary Report on Patentability dated Oct. 1, 2015 issued by WIPO in International Patent Application No. PCT/IB2013/052296 filed on Mar. 22, 2013, which is the corresponding International Application which the present application is a National Phase of.

* cited by examiner

*Primary Examiner* — Audrea Buckley
(74) *Attorney, Agent, or Firm* — Porzio Bromberg & Newman P.C.

(57) ABSTRACT

The present invention relates to process for preparing cosmetic compositions at two stages. The first relates to the preparation of organogels in which liquid oils are structured by a mixture of structuring agents such as monoglycerides and waxes, which also have the addition of other components such as polymers and polyol esters. The second step is the formation of the cold or hot process cosmetic compositions where emulsions are prepared by the addition of water, aqueous solutions and other components, to the organogel. The emulsions prepared have superior sensory, chemical-physical and stability characteristics, to those currently produced by the classic technology of preparation with emulsifiers.

21 Claims, 3 Drawing Sheets

STRUCTURING OF COSMETIC COMPOSTION USING ORGANOGELS

FIELD OF THE INVENTION

The present invention relates to a cold and hot process of structuring of cosmetic compositions. More specifically, the present invention relates to a process for the preparation of cosmetic compositions, in that, initially organogels are prepared, which besides the usual components such as organic liquids to be structured and structuring agents, are added natural or synthetic polymers and/or polyol esters. Thus, the organogels prepared are the base for cold and hot process of structuring cosmetic compositions upon the addition of water, aqueous solutions or other active components or not.

BACKGROUND OF THE INVENTION

Emulsions

Emulsions are dispersed systems consisting of two immiscible liquid phases (oil and water), where the dispersed or internal phase is finely divided and distributed in another external or continuous phase.

The conventional emulsions are classified in oil/water (O/W) when the oil droplets are dispersed in water and water/oil (W/O), when water droplets are dispersed in oil. It is important to clarify that by "oil" is considered all nonpolar hydrophobic liquids and by "water" is considered all highly polar hydrophilic liquids.

In principle, oil and water phases are made up of only one substance, however, in cosmetic preparations, each phase usually contains a variety of "components". The viscosity of the emulsion and its appearance are controlled, in part, by the type of emulsion, the particle size of the dispersed phase and the ratio between the internal and external phases. The system is thermodynamically unstable; the particle size can vary once the internal phase constantly tries to agglomerate and separate forming a second phase.

Polymers and emulsifiers are used to delay this inevitable separation. During the process of the emulsion formation, these compounds can be adsorbed in the oil-water or water-oil interface. Depending upon the agent used and by the reduction of interfacial tension, it promotes the stabilization of finely divided droplets and controls the type of emulsion formed (W/O or O/A).

Organogels

Organogels are defined as thermoreversible three-dimensional gel network that immobilizes an organic fluid creating a material with characteristics and rheological properties of a solid, but with greater part of its composition being liquid. They can also be defined as a viscoelastic material composed by a structuring agent and a nonpolar liquid phase. They are semisolid systems where an oil phase is immobilized by a self-assembled three dimensional network formed by the structuring agent. The liquid phase may be a polar organic solvent (such as benzene, hexane, etc.), mineral oil or vegetable oil.

Several chemical compounds are able to structure organic liquids forming organogels. Some examples are sterols, lecithins, mono- and diglycerides, lecithin mixtures with sorbitan esters, fatty acids and fatty alcohols and waxes and wax esters.

The potential applications of organogels in food, pharmaceutical, cosmetic and petrochemicals industries have raised the interest in this type of material. The interest is partly due to the great diversity of possible mesoscopic and microscopic structures. In the food industry there is a great potential for the use of organogels. It can be used to minimize oil migration in food with multiple components, for example, chocolates. Can also be used to structure edible oils, consequently reducing the use of saturated and trans fat. The organogel technology has also been applied in the pharmaceutical field to structure dermal and transdermal products and as transporter or carrier system for topical drugs or therapeutic substances. In the petrochemical industry there are investigations to study the possibility to contain oil spills using gelation phase of the selective organogels, and also gelation of flammable solvents for storage and transportation. They have been also used in the preservation of works of art, where the solvents used to clean oil paintings are gelled in order to prevent its penetration in original layers of paint and prevent damage to the work.

The structuring of oil has recently been applied in the cosmetic industry as structurers for personal care products. It is also known that waxes are applied in structuring oily bases for lipstick, "gloss", eyeliners, lip balms, etc. Structured emulsions are part of a different scope of organogels. These emulsions refer to structured oils by structuring agents, which, due to their amphiphilic nature, allow the incorporation of a significant amount of water.

BRIEF DESCRIPTION OF THE FIGURES

The illustrative figures attached, shows the micrographs of examples of cosmetic compositions according to the present invention. It should be considered, however, that such illustrations do not serve to limit or define the overall scope of the invention. The figures are.

BRIEF SUMMARY OF THE INVENTION

Figure 1:
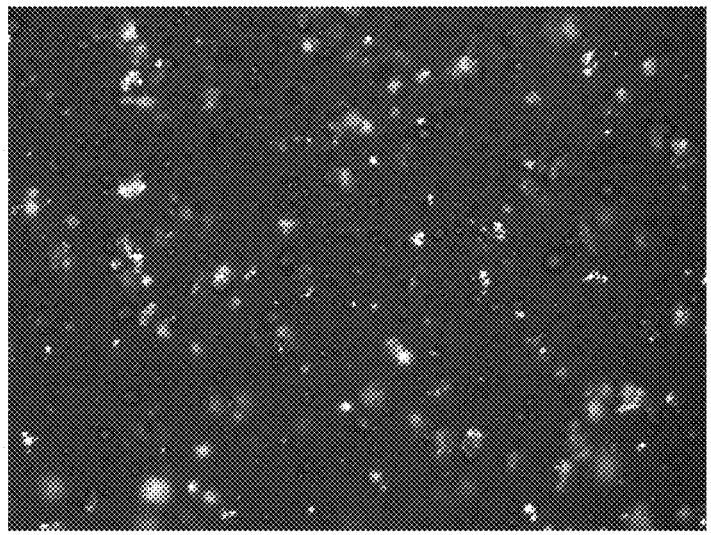
FIG. 1—Polarized Light Microscopy of an emulsion prepared from Organogel 1 (3%) in water (97%). Oil in water emulsion (O/W).

The cold or hot process preparation of cosmetic compositions, according to the present invention, comprises two basic steps. The first step is the preparation of the organogels in which liquid oils are structured by a mixture of monoglycerides and waxes as structuring agents, which also have the addition of other components as polymers and polyol esters. The second step is the formation of cold process cosmetic compositions where emulsions are prepared by the addition of water, aqueous solutions and other components, to the organogel. The emulsions formed have superior sensory effect, chemical-physical characteristic and stability, to those currently produced by the classic technology of preparation with emulsifiers prior art.

DETAILED DESCRIPTION OF THE INVENTION

The process, according to the present invention, is intended to cold or hot process cosmetic compositions, which include: oil in water (O/W), water in oil (W/O) and lamellar emulsion using a two-step process. The first step involves the preparation of the oily base that is structured by a mixture of compounds containing waxes, monoglycerides, polymers, and esters of polyols, in the form of organogel. Unlike conventional emulsions, where the oil phase is in liquid form, according to the present invention, the oil phase is structured in the form of an organogel. In a second step, named step of emulsification, the organogel formed is used as a base for the emulsion process. The emulsion is then formed by the addition of water, aqueous solutions and/or other components of the cosmetic composition, in the organogel.

The structuring agent is formed by a mixture of vegetable, animal, mineral or synthetic waxes, with monoglycerides, and their mixtures, also from vegetable, animal and/or synthetic sources. The organogels may also have in its composition, natural and/or synthetic polymers and polyols esters such as glycerol, xylitol, sorbitol and/or mannitol, as an improver in the process of structuring the emulsion. The characteristics of the organogel formed will be defined by the proportion of each component, where the innovation is the incorporation of the oil phase not in the liquid form but as an organogel (solid-like material). This is done by a cold or hot process in a second step of the process. The synergism of the structuring agents and other components from the cosmetic composition, confer unique characteristics to the organogel and the resulting emulsions.

The concentration of structuring agent and other components of organogel depend on the type of emulsion being prepared. Typically, it varies from 0.2 to 70%. The same happens with the other components of the cosmetic composition. The concentration of wax in the organogel is in the range of 0 to 20%, preferably between 0.5% and 12%, or more precisely between 1 and 5%. The concentration of monoglycerides in the organogel is in the range of 0 to 25%, preferably between 2 and 18%, or more precisely between 10 and 15%. The concentration of polymers in the organogel is in the range of 0 to 40%, preferably between 5% and 30%, or more precisely between 15 and 25%. The concentration of polyol in the organogel is in the range of 0 to 40%, preferably between 0.1 and 30%, or more precisely between 0.2 and 20%.

The organic fluid being structured by structuring agents can be any type of vegetable, animal, mineral or synthetic oil and its concentration may be in the range of 30 to 99% of organogel components.

The organogel is prepared by mixing organic fluid (oil) with the structuring agents. The oil is heated to between 60 and 95° C. and structuring agents are added as well as other structural components such as polymers and polyol esters, and are mixed until complete dissolution. The organogel is formed during cooling of the mixture. The cooling process can be performed at cooling rates of 1° C. per hour to 5° C. per minute and temperatures can vary between 25° C. (room temperature) and −5° C., depending on the desired structure. After the cooling process and formation of organogel, it is stored at temperatures between 5 and 40° C.

The organogel formed is an oily base used to prepare the emulsion in the second step of the process, in which water and other aqueous or non-aqueous ingredients, active or not, will be added and emulsified. The resulting cosmetic compositions, and as described in the present invention, the oil phase of the emulsion is not in the liquid form usually stabilized by an emulsifier, but rather as an organogel, structured by a mixture of structuring agents and which contains other components such as polymers and polyol esters. The concentrations of organogel, water, aqueous solutions and other components to be used in the cold or hot process of the emulsion depend on the characteristics desired in the cosmetic final product.

The organogel prepared according to the present invention can be applied in a variety of body care products or any cosmetic product that requires formation of emulsions, be them oil-in-water (O/W), water in oil (W/O) or, lamellar emulsions. These applications generate products with stability and sensory characteristics differentiated. There is not a maximum or a minimum concentration of the organogel to be used, but their concentration may vary from 0.1 to 20%, preferably between 0.5 and 10% or more precisely between 2 and 8%. The concentration should be chosen according to the desired composition or viscosity of the final product.

Illustrative examples, whether the organogels, mixtures of structural and other components of the cosmetic compositions that were formulated and processed under the conditions given below, serve to better describe the present invention. However, the data and procedures presented merely refer to some forms of application of the present invention and should not be taken as limiting the scope thereof.

EXAMPLES

Example 1. Organogel 1 Preparation

The Organogel 1 was prepared by combining high oleic sunflower oil (HOSO) as the organic fluid, that was structured with candelilla wax and glyceryl monostearate (monoglyceride) as structuring agents and Xylityl Sesquicaprylate (polyol esters) and sodium polyacrylate (polymer) as auxiliary compounds in stabilizing the emulsion. The emulsion will be prepared using the organogel in the second step of the process. The high oleic sunflower oil, candelilla wax esters, xylitol, glyceryl monostearate and sodium polyacrylate are mixed (500 rpm) and heated (80° C.) until the complete melting of all components. After incorporation of the ingredients in the oil, the mixture is stirred for 10 minutes at 1.400 rpm. At the end of the process the mixture is cooled to room temperature (25° C.) to allow the formation of organogel being stored at 8° C.

In the formulation of Organogel 1 were used components and concentrations listed in Table 1.

TABLE 1

| Composition of Organogel 1 | |
| --- | --- |
| Ingredients | % (weight) |
| High Oleic Sunflower Oil | 59.95 |
| Sodium Polyacrylate | 25.00 |
| Glyceryl Stearate | 13.00 |
| Candelilla Wax | 2.00 |
| Tocopherol | 0.05 |

Example 1A. Preparation of Oil/Water Emulsions (O/W) Using the Organogel 1

The Organogel 1 was used to prepare oil in water emulsion by simply dispersing Organogel 1 in water with no heating. The emulsion was prepared by combining 3% of Organogel 1 with 97% of water. There is no need for high mechanical agitation to achieve good dispersion and stability of the resulting emulsion. The dispersion of Organogel 1 in water forms an emulsion in which stability is conferred by the gelation of aqueous continuous phase and the oily dispersed phase. Gelation of the dispersed and continuous phases increases the viscosity of the medium retarding thereby agglomeration of the dispersed phase and avoiding phase separation, which increases stability. The presence of the oily phase as organogel, and not as a liquid, can be confirmed by the presence of monoglyceride crystals (glyceryl monostearate) and wax (candelilla wax) within the oil globules, which is clearly shown in FIG. 1. The polarized light microscopy was used to verify the presence of these crystals (monoglycerides and waxes inside the oil gelled globules) which act as structuring agents. These crystals, during the preparation process of the organogel in the cooling step, are organized forming a crystal lattice able to sustain the oil phase and to maintain the globule structure.

Figure 2:
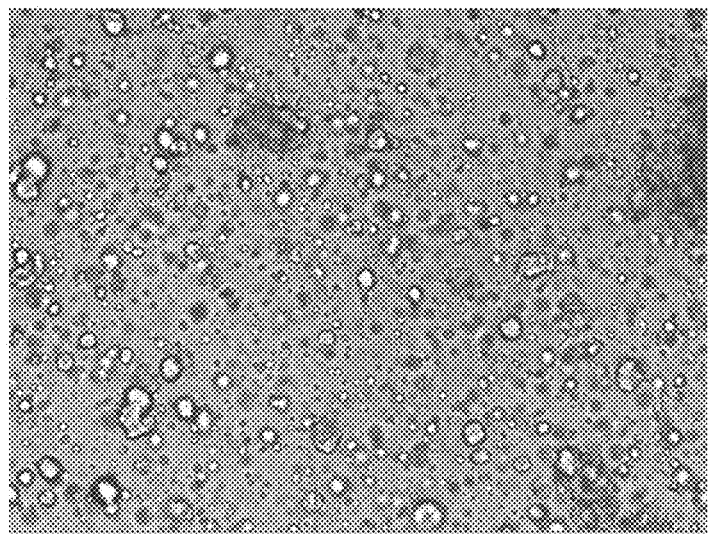
FIG. 2—Optical microscopy of an emulsion prepared from Organogel 1 (3%) in water (97%). Oil in water emulsion (O/W).

It is well known that liquid oil, when emulsified in water, is dispersed in small droplets with a well defined rounded shape. In this case, as can be seen in FIG. 2, the oil droplet has not a rounded shape, further confirming its characteristic of a gel.

The viscosity of the emulsion obtained was more than $5 \cdot 10^4$ cps (Brookfield LV, spindle TF), with a uniform distribution of particle size. The distribution of the globules of the emulsion formed with organogel can be seen in FIG. 2, where the optical microscopy was used to verify the type, dispersion and stability of the emulsion. The application of Organogel 1 in water enables the formation of emulsions with excellent sensory attributes.

Example-1B. Preparation of a Body Lotion Using Organogel 1

The following example describes the preparation of a cosmetic composition (body lotion) where Organogel 1 was applied at a concentration of 3%. Table 2 lists the ingredients used in the cosmetic formulation. In the process of obtaining the lotion, the components in phase 2 were first combined with Organogel 1 (step 1). This combination was made by a simple mixing of the two phases until the organogel had been completely dispersed, forming a homogeneous phase. Under moderate mechanical stirring (500 rpm) the third phase, which contained water, and the fourth phase were incorporated into the mixture. The mixture was stirred for 15 minutes until the formation of a homogeneous emulsion.

TABLE 2

Cosmetic composition (Body lotion) prepared with Organogel 1

| Ingredients | % (weight) |
|---|---|
| PHASE 1 | |
| Organogel 1 | 3.00 |
| PHASE 2 | |
| Mineral Oil | 13.00% |
| Isopropyl Palmitate | 2.00% |
| Dimethicone | 0.20% |
| PHASE 3 | |
| Glycerin | 2.00% |
| Water | q.s.p. 100.00 |
| PHASE 4 | |
| Preservative | 0.50% |

The oil in water emulsion obtained had high viscosity ($>5 \cdot 10^4$ cps), white color, and excellent gloss with a soft and pleasant feeling when applied to skin. The Organogel 1 proved to be effective when used to help the dispersion of an oil phase in water, even with an extra load of oil (phase 2) of 15%. The structure of Organogel 1 was suitable for forming a fine dispersion of globules. The emulsion stability tests revealed fully satisfactory results regarding viscosity and pH stability as shown in Table 3.

TABLE 3

Stability of Viscosity and pH results of lotion prepared using Organogel 1

| | |
|---|---|
| INITIAL VISCOSITY (cps) | 48.230 |
| VISCOSITY AT ROOM TEMPERATURE (30 DAYS) | 46.140 |
| VISCOSITY AT 45° C. (30 DAYS) | 51.935 |
| INITIAL pH | 6.27 |
| pH AT ROOM TEMPERATURE (30 DAYS) | 6.20 |
| pH AT 45° C. (30 DAYS) | 6.22 |

Example-1C. Preparation of a Sunscreen Formulation Using Organogel 1

The sunscreen, which formulation is described in Table 4, is another example where the Organogel 1 can be applied. In this case, the emulsion was prepared following the procedure described in the previous example (1B). However, in this process, the components from phase 2, because they are solid, had to be melted and added, at a temperature of 40° C., to phase 1 that comprises the Organogel 1. The formation of the oil in water emulsion was made by a cold process (T=25° C.) with stirring. As described in Example 1B, there is no need for high agitation.

TABLE 4

Cosmetic composition (sunscreen) prepared from Organogel 1

| Ingredients | % (weight) |
|---|---|
| PHASE 1 | |
| Organogel 1 | 3.0 |
| PHASE 2 | |
| C8-C10 Triglycerides | 5.0 |
| Octyl Methoxycinnamate | 5.0 |
| PHASE 3 | |
| Glycerin | 2.0 |
| Water | q.s.p. 100.0 |
| PHASE 4 | |
| Preservatives | 0.5 |

The results showed excellent physical and chemical stability of this cosmetic emulsion as shown in Table 5.

TABLE 5

Viscosity and pH stability of a sunscreen formulation prepared using Organogel 1.

| | |
|---|---|
| INITIAL VISCOSITY (cps) | 56.295 |
| VISCOSITY AT ROOM TEMPERATURE (30 DAYS) | 55.515 |
| VISCOSITY AT 45° C. (30 DAYS) | 55.410 |
| INITIAL pH | 6.29 |
| pH AT ROOM TEMPERATURE (30 DAYS) | 6.20 |
| pH AT 45° C. (30 DAYS) | 6.12 |

Example-1D. Preparation of Hydroalcoholic Gels Using Organogel 1

This example describes the preparation of hydroalcoholic gels using Organogel 1. The preparation of oil in water emulsion is made from the mixture of phases 1 and 2, according to the concentrations listed in Table 6. Phase 3 was subsequently incorporated, under mechanical stirring. The emulsion was prepared to evaluate the efficiency of the Organogel 1 to maintain the emulsion stable when different polar solvents such as ethanol, in concentrations of up to 30% are added to the emulsion. The emulsion formed was stable for 30 days at 45° C. for ethanol concentrations ≤30%.

TABLE 6

Cosmetic composition (hydroalcoholic gel) prepared with Organogel 1.

| Ingredients | % (weight) |
|---|---|
| PHASE 1 | |
| Organogel 1 | 3.0 |
| PHASE 2 | |
| Water | 67.0 e 83.0 |
| PHASE 3 | |
| Ethyl Alcohol (96° GL) | 15.0 e 30.0 |

The examples described above demonstrate the ability of Organogel 1 to form stable oil in water (O/W) emulsions. The emulsions were readily prepared at low temperature (room temperature), showed high stability, excellent appearance and high moisturizing effect.

Example-2. Organogel 2 Preparation

This example describes the formulation of a product which is referred to as Organogel 2 and has a similar composition to Organogel 1 (as seen in Table-1) but with addition of 0.2% of polyol esters (Xylityl Sequicaprylate) as Table 7. Candelilla wax, high oleic sunflower oil, glyceryl monostearate and xylitol esters were mixed (500 rpm) and heated (80° C.) until complete melting of all components. Under high agitation, the sodium polyacrylate polymer was slowly added to the mixture. The mixture was cooled to permit formation of organogel.

TABLE 7

Organogel 2 Composition

| Ingredients | % (weight) |
|---|---|
| High Oleic Sunflower Oil | 59.75 |
| Sodium Polyacrylate | 25.00 |
| Glycerol Stearate | 13.00 |
| Candelilla Wax | 2.00 |
| Xylityl Sesquicaprylate | 0.20 |
| Tocopherols | 0.05 |

Figure 3:
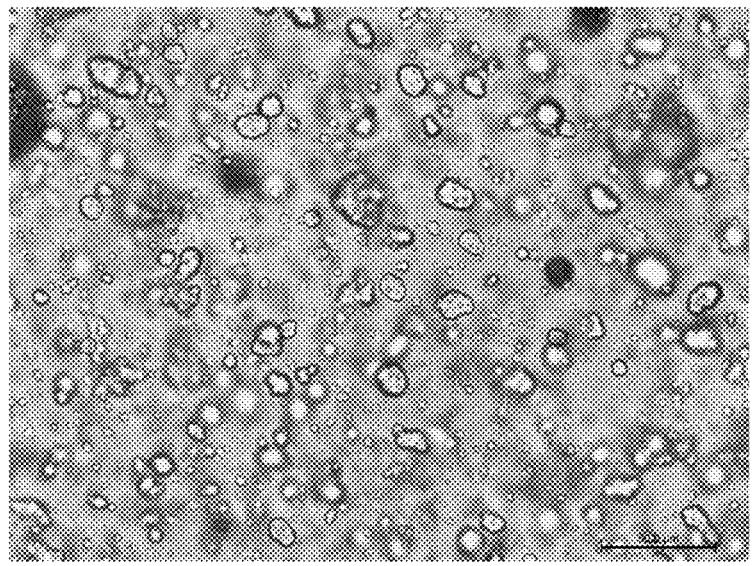
FIG. 3—Optical microscopy of an emulsion prepared from Organogel 2 (3%) in water (97%). Lamellar emulsion.

Despite the small concentration of xylitol esters (0.2%), it is observed that it has a significant influence on the formation and stabilization of cold process emulsions with characteristics superior to conventional emulsions including emulsions prepared with Organogel 1. The addition of xylitol esters is responsible for the formation of a structure different from that observed in Example 1, as can be seen in FIG. 3. It was observed the presence of a lamellar structure, where the globules of organogel (disperse phase) in the emulsion are stabilized by a structure composed of layers of lamellar structuring. This reflects strongly and positively in the appearance of the resulting emulsion. Emulsions formed were whiter and less translucent.

Example-2A. Preparation of Oil/Water (O/W) Lamellar Emulsions From the Organogel 2

The Organogel 2 was used to prepare an oil in water cold emulsion (O/W), merely by dispersing the Organogel 2 (3%) in water (97%). The dispersion of Organogel 2 in water forms an emulsion with differentiated characteristics. The globules of oil show to have inside, a lamellar structure, which results in an emulsion of high sensory quality, superior to traditional emulsions produced by a hot process, or even the other cold process emulsions, which use emulsifiers and oil liquid phases. Gelation of the dispersed and continuous phases increases the viscosity of the emulsion, thus slowing the agglomeration of the dispersed phase and, thereby, avoiding the phase separation. There was no need for high mechanical agitation to achieve good dispersion and stability of the oil phase in the aqueous phase.

The Organogel 2 can be applied to manufacture a wide variety of body-care products, cosmetics or any other product that require the formation of oil in water emulsion. These applications generate products with superior sensory characteristics when compared to other cold process emulsions. There is not maximum or minimum concentration of Organogel 2 to be dispersed in water. It is recommended between 3-5% for lotions with viscosity of about 30,000 to 70.000 cps.

Example-2B. Preparation of Moisturizing Lotion Using Organogel 2

The cosmetic composition of a moisturizing lotion, where Organogel 2 was applied, is shown in Table 8. In the process of obtaining the lotion, the components of phase 2 were primarily combined with the phase 1 (organogel). This combination was made by a simple mixing (low shear) of the two phases, with a complete dispersion of the organogel in the oil phase, to form a homogeneous phase. Under moderate mechanical stirring (500 rpm) stages 3 and 4 were incorporated into the mixture. The mixture was stirred continuously until the formation of a homogeneous emulsion (15 minutes).

The emulsion formed presented adequate viscosity for this type of product, white color, excellent gloss and a smooth sensory touch when applied to the skin. Despite the low concentration of xylitol esters in Organogel 2, its addition contributes to improve and facilitate oil dispersion as well as the appearance and sensory effect of the resulting emulsion. The determination of emulsion stability proved fully satisfactory results regarding the appearance, viscosity and pH, as shown in Table 9.

TABLE 8

Composition cosmetics (Lotion) prepared with 2 Organogel

| Ingredients | % (weight) |
|---|---|
| PHASE 1 | |
| Organogel 2 | 3.0 |
| PHASE 2 | |

TABLE 8-continued

Composition cosmetics (Lotion) prepared with 2 Organogel

| Ingredients | % (weight) |
|---|---|
| Mineral Oil | 13.0 |
| Isopropyl Palmitate | 2.0 |
| Dimethicone | 0.2 |
| PHASE 3 | |
| Glycerin | 2.0 |
| Water | q.s.p. 100.00 |
| PHASE 4 | |
| Preservative | 0.5 |

TABLE 9

Viscosity and pH stability of the lotion prepared from Organogel 2

| | |
|---|---|
| INITIAL VISCOSITY (cps) | 30.515 |
| VISCOSITY AT ROOM TEMPERATURE (30 DAYS) | 26.650 |
| VISCOSITY AT 45° C. (30 DAYS) | 29.105 |
| INITIAL pH | 6.30 |
| pH AT ROOM TEMPERATURE (30 DAYS) | 6.21 |
| pH AT 45° C. (30 DAYS) | 6.29 |

Example-3. Organogel 3 Preparation

The organogel prepared by combining the ingredients described in Table 10 will be referred to as Organogel 3. The preparation of Organogel 3 was also performed as described in Examples 1 and 2. The difference, in this case, is the concentration of the polyol esters (Xylityl Sesquicaprylate). It is important to mention that, when the concentration of esters of xylitol is increased or decreased in the formulation, the proportion of total, or part, of the components can be changed. The formulation of Organogel 3 was developed for the preparation and stabilization of lamellar cold process emulsions as described in the following examples.

TABLE 10

Composition of the Organogel 3

| Ingredients | % (weight) |
|---|---|
| High Oleic Sunflower Oil | 50.0 |
| Xylityl Sesquicaprylate | 2.0-40.0 |
| Sodium Polyacrylate | 15.0 |
| Glyceryl Stearate | 13.0 |
| Candelilla Wax | 2.0 |

Example-3A. Preparation of Lamellar Oil/Water (O/W) Emulsions Using the Organogel 3

Figure 4:
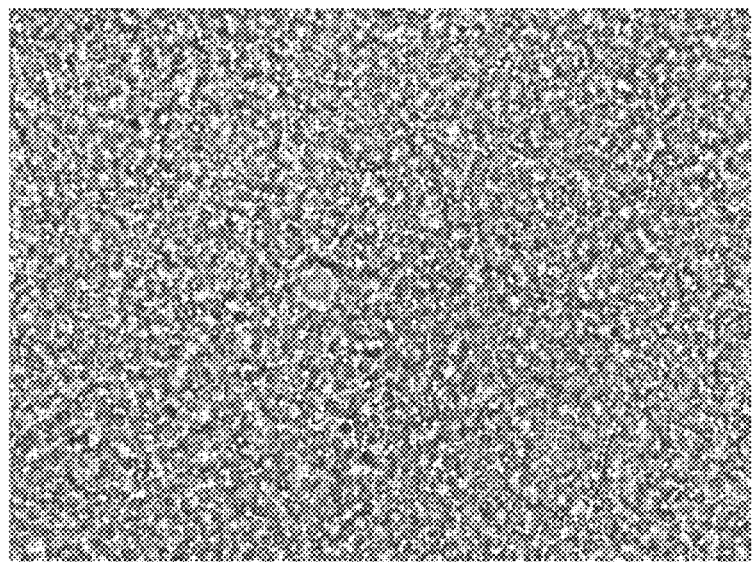
FIG. 4—Optical microscopy of the emulsion prepared from Organogel 3 (3%) in water (97%). Lamellar emulsion.

The ability of Organogel 3 in developing lamellar emulsions was demonstrated. In this example, 3% of Organogel 3 and 97% water were mixed slowly under moderate agitation (500 rpm). After the emulsion being formed, it was homogenized for 10 minutes. With the addition of Xylityl Sesquicaprylate to the organogel, it was observed the formation of an oil in water emulsion, where the dispersed cells of the organogel showed a different form of structure, a lamellar structure within the globule, as seen in Example 2. This different way of structuring, conferred a higher quality than the emulsion formed in terms of dispersion and sensory effect. This behavior was observed when the concentration of Xylityl Sesquicaprylate ranged from 2 to 40% in the organogel formulation. However, it also was noticed that, when a high concentrations of Xylityl Sesquicaprylate (20-40%) is used in the formulation of Organogel 3 and this is dispersed in a greater concentration of oil phase, lamellar emulsions are generated and the oil phase (organogel) is retained within lamellae, as seen in FIG. 4.

This organogel, as well as all others previously described, can be used for the preparation of a number of hygiene products and body care, as in the example described below.

Example-3B. Preparation of Facial Cream Using Organogel 3

The composition described in Table 11 illustrates the use of Organogel 3 as a base in the preparation of a facial cream. As described in Example 1B, the components of phase 2 were previously combined with phase 1, as well as the components of phase 3 and 4. The two mixtures were then combined and mixed under mechanical stirring. The process was conducted at room temperature.

TABLE 11

Cosmetic Composition (Facial Cream) prepared with Organogel 3

| Ingredients | % (weight) |
|---|---|
| PHASE 1 | |
| Organogel 3 | 5.0 |
| PHASE 2 | |
| LANOL 99 | 3.0 |
| *Astrocaryum* sp. Fat | 1.0 |
| Alkyl Benzoate C12-C15 | 2.0 |
| *Bidens pilosa* extract | 3.0 |
| PHASE 3 | |
| Glycerin | 2.0 |
| Water | q.s.p. 100.0 |
| PHASE 4 | |
| Preservative | 0.50 |
| PHASE 5 | |
| Triethanolamine pH (6.4-7.5) | q.s.p. |

The lamellar emulsion generated by the presence of Organogel 3, which contained high concentration Xylityl Sesquicaprylate, resulted in a new microstructure of the emulsions. Unlike the conventional microstructure of oil in water emulsions, in this case the oil phase, in the form of an organogel, was located on the external interface of the globule forming a lamellar structure. This is part of a more complex definition, where the oil phase is surrounded by several layers containing the structuring agent. The main characteristics of the emulsion prepared with Organogel 3 are, the appearance and the sensory effect (with a no tack touch). Table 12 shows the results of the viscosity and the pH during stability test of the lamellar emulsion formed in the facial cream formulation. Results were considered satisfactory to such cosmetic composition.

TABLE 12

Viscosity and pH stability of lotion prepared from Organogel 3.

| | |
|---|---|
| INITIAL VISCOSITY (cps) | 35.805 |
| VISCOSITY AT ROOM TEMPERATURE (30 DAYS) | 32.060 |
| VISCOSITY AT 45° C. (30 DAYS) | 35.960 |

TABLE 12-continued

Viscosity and pH stability of lotion prepared from Organogel 3.

| | |
|---|---|
| INITIAL pH | 7.41 |
| pH AT ROOM TEMPERATURE (30 DAYS) | 7.01 |
| pH AT 45° C. (30 DAYS) | 6.40 |

Example-4. Preparation of Organogel 4

The combination and concentrations of ingredients listed in Table 13 will be referred to as Organogel 4. The organogel was specially formulated for preparing water in oil (W/O) cold process emulsions, by incorporating in the organogel the surfactant Polyglycerol Polyricinoleate, a polyol ester. This organogel was prepared just as illustrated previously, except for the addition of the Polyglycerol Polyricinoleate that happens in the end of the process. The organogel obtained had excellent texture and a fine monoglyceride and wax crystallization.

TABLE 13

Composition of the Organogel 4

| Ingredients | % (weight) |
|---|---|
| High Oleic Sunflower Oil | 44.6 |
| Polyglycerol Polyricinoleate | 25.0 |
| Sodium Polyacrylate | 18.7 |
| Glycerol Stearate | 9.6 |
| Candelilla Wax | 1.7 |

The ability of the Organogel 4 in forming water-in-oil (W/O) emulsions is shown in Examples 4A and 4B described below.

Example-4A. Water in Oil Emulsion (W/O) Prepared Using Organogel 4

Figure 5:
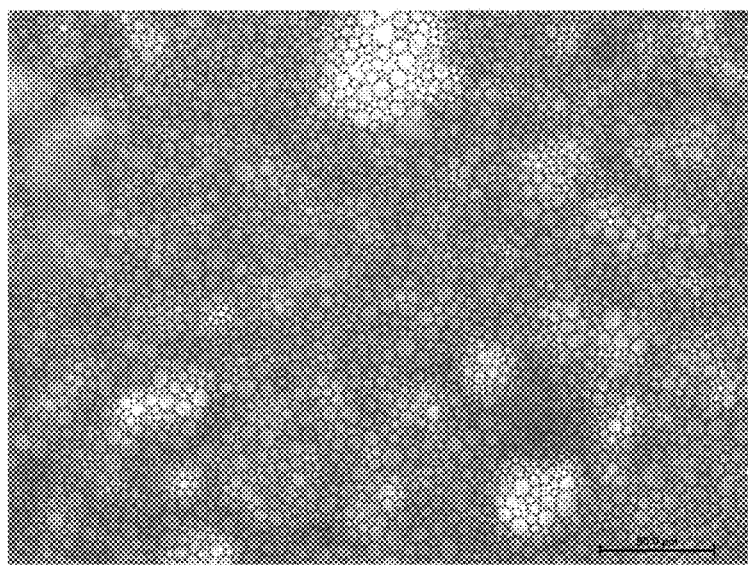
FIG. 5—Optical microscopy of the emulsion prepared from Organogel 4 (3%) in water (97%). Water in oil emulsion (W/O).

In this example, 3% of Organogel 4 and 97% of water were mixed under high agitation (1400 rpm). After the emulsion being formed it was homogenized for 10 minutes to ensure good dispersion. Given the small concentration of Organogel 4 and hence a lower concentration of nonpolar phase (continuous phase of the emulsion water in oil), the emulsion formed had a high viscosity, being greater than 3.105 cps (Brookfield LV—spindle TF). The emulsion formed was characterized by a unique touch combined with a moisturizing effect, a refreshing feeling due to water in gel form and a final touch of softness without being overly oily. The combination of water and Organogel 4 creates better distribution of the water droplets which also help to increase the stability of the emulsion. The process was conducted at room temperature (cold process), and the microstructure of the emulsion is shown in FIG. 5, that is characteristic of water in oil emulsion.

Example-4B. Preparation of Sunscreen SPF 30 Using 4 Organogel

The Organogel 4 was used as the base for the preparation of an SPF 30 sunscreen whose formulation is described in Table 14. In their preparation, the components of phases 2 were first combined with the first phase. Phase 2 was melted and cooled to 40° C. before incorporation of phase 1. Under high mechanical stirring (1400 rpm) phase 3 was slowly incorporated into the mixture.

TABLE 14

Cosmetics composition (Sunscreen SPF 30) prepared with Organogel 3

| Ingredients | % (weight) |
|---|---|
| PHASE 1 | |
| Organogel 4 | 3.0 |
| PHASE 2 | |
| C12-C15 Alkyl Benzoate | 1.0 |
| Octyl Methoxycinamate | 8.0 |
| Uvinul T-150 | 4.0 |
| Tinosorb S | 3.0 |
| Parsol TX 50 AB | 6.0 |
| Preservative | 0.05 |
| PHASE 3 | |
| Glycerin | 2.0 |
| Water | q.s.p. 100.0 |
| Tinosorb M | 2.0 |

The sunscreen prepared with Organogel 4 showed initial viscosity of 155,500 cps. After 30 days of storage at room temperature the viscosity remained at 148,750 cps.

The invention claimed is:

1. A structuring process of a cosmetic composition comprising two basic steps, the first step (i) being the structuring of an oil with one or more structuring agents, the one or more structuring agents being selected from natural, vegetable, animal, mineral and synthetic waxes in concentrations ranging from 0.5% to 20% or monoglycerides, diglycerides, and their mixtures thereof, from vegetable, animal and/or synthetic sources in concentrations of 2 to 25% to form a solid organogel and the second step (ii) being the structuring of a cold or hot process to form an emulsion, said cold or hot process comprising adding an aqueous phase to the organogel formed in the first step (i), with or without the addition of other components, the organogel comprising the one or more structuring agents within an oil gelled phase.

2. The structuring process of a cosmetic composition according to claim 1, wherein the cosmetic compositions are water in oil emulsions (W/O), oil in water (O/W) emulsions, or lamellar depending on the one or more structuring agents selected and the concentration of the one or more structuring agents.

3. The structuring process of a cosmetic composition according to claim 2, wherein the emulsions comprise organogel concentrations between 0.1 and 20%.

4. The structuring process of cosmetic compositions according to claim 1, wherein the organogel comprises a mixture of the oil, the one or more structuring agents and auxiliary structuring agents.

5. The structuring process of a cosmetic composition according to claim 1, wherein the aqueous phase comprises only water or aqueous solutions containing propylene glycol, butylene glycol, and glycerin.

6. The structuring process of a cosmetic composition according to claim 1, wherein the oil comprises vegetable, animal, mineral and/or synthetic oils in concentrations ranging from 30 to 99%.

7. The structuring process of a cosmetic composition according to claim 4, wherein the auxiliary structuring agents comprise natural and/or synthetic polymers in concentrations of 5 to 40%.

8. The structuring process of cosmetic compositions according to claim 7, wherein the auxiliary structuring agents comprise natural or synthetic esters of polyols chosen from glycerol, xylitol, sorbitol and mannitol in concentrations of 0.1-40%.

9. The structuring process of a cosmetic composition according to claim 1, wherein the composition further comprises Xylityl Sesquicaprylate as the enhancer of the physical and sensory characteristics of structured cosmetic composition.

10. The structuring process of a cosmetic composition according to claim 1, wherein the structuring process of the organic fluid forming the organogel comprises:
   a) heating the oil to 60-95° C.,
   b) adding and mixing the structuring agents until dissolution is complete and other auxiliary structural components,
   c) cooling the mixture at rates 1° C. per hour to 5° C. per minute, at temperatures ranging from 25° C. and −5° C. to achieve a solid state,
   d) storing the organogel at temperatures of 5 to 40° C.

11. The structuring process of a cosmetic composition according to claim 1 wherein it is applied to obtain lotion, sunscreen, after sun products, hydroalcoholic gels, facial cream and gel cream.

12. The structuring process of a cosmetic composition according to claim 2, wherein the emulsions comprise organogel concentrations between 0.5 and 10%.

13. The structuring process of a cosmetic composition according to claim 2, wherein the emulsions comprise organogel concentrations between 2 and 8%.

14. The structuring process of a cosmetic composition according to claim 1, wherein the one or more structuring agents comprise natural, vegetable, animal, mineral and/or synthetic waxes in concentrations ranging from 0.5 to 12%.

15. The structuring process of a cosmetic composition according to claim 4, wherein the one or more structuring agents comprise natural, vegetable, animal, mineral and/or synthetic waxes in concentrations ranging from 1 to 5%.

16. The structuring process of a cosmetic composition according to claim 14, wherein the one or more structuring agents comprise monoglycerides, diglycerides, and mixtures thereof, from vegetable, animal and/or synthetic sources in concentrations of 2 to 18%.

17. The structuring process of a cosmetic composition according to claim 14, wherein the one or more structuring agents comprise monoglycerides, diglycerides, and mixtures thereof, from vegetable, animal and/or synthetic sources in concentrations of 10 to 15%.

18. The structuring process of a cosmetic composition according to claim 14, wherein the auxiliary structuring agents comprise natural and/or synthetic polymers in concentrations of 5 to 30%.

19. The structuring process of a cosmetic composition according to claim 14, wherein the auxiliary structuring agents comprise natural and/or synthetic polymers in concentrations of 15 to 25%.

20. The structuring process of a cosmetic composition according to claim 5, wherein the auxiliary structuring agents contain natural or synthetic esters of polyols, chosen from glycerol, xylitol, sorbitol and/or mannitol in concentrations of 0.1 to 30%.

21. The structuring process of cosmetic compositions according to claim 5, wherein the auxiliary structuring agents contain natural or synthetic esters of polyols, chosen from glycerol, xylitol, sorbitol and/or mannitol in concentrations of 0.2 to 20%.

* * * * *